US010603228B2

(12) United States Patent
Manabe et al.

(10) Patent No.: US 10,603,228 B2
(45) Date of Patent: Mar. 31, 2020

(54) UNDERPANTS-TYPE DISPOSABLE DIAPER

(71) Applicant: DAIO PAPER CORPORATION, Ehime (JP)

(72) Inventors: Sadanao Manabe, Tokyo (JP); Tomotsugu Matsui, Ehime (JP); Akinori Fukae, Tokyo (JP); Kosuke Murai, Ehime (JP)

(73) Assignee: Daio Paper Corporation, Ehime (JP)

( * ) Notice: Subject to any disclaimer, the term of this patent is extended or adjusted under 35 U.S.C. 154(b) by 359 days.

(21) Appl. No.: 15/519,748

(22) PCT Filed: Oct. 16, 2015

(86) PCT No.: PCT/JP2015/079318
§ 371 (c)(1),
(2) Date: Apr. 17, 2017

(87) PCT Pub. No.: WO2016/063804
PCT Pub. Date: Apr. 28, 2016

(65) Prior Publication Data
US 2017/0231836 A1    Aug. 17, 2017

(30) Foreign Application Priority Data
Oct. 24, 2014 (JP) ................................. 2014-217524

(51) Int. Cl.
*A61F 13/494* (2006.01)
*A61F 13/496* (2006.01)
*A61F 13/49* (2006.01)

(52) U.S. Cl.
CPC .......... *A61F 13/494* (2013.01); *A61F 13/496* (2013.01); *A61F 13/49413* (2013.01);
(Continued)

(58) Field of Classification Search
CPC ............ A61F 13/49413; A61F 13/4942; A61F 13/494; A61F 13/496; A61F 2013/49092;
(Continued)

(56) References Cited

U.S. PATENT DOCUMENTS 5,476,458 A * 12/1995 Glaug ............... A61F 13/15203
604/358
8,377,026 B2 * 2/2013 Mishima ........... A61F 13/15593
156/202

(Continued)

FOREIGN PATENT DOCUMENTS

JP    2002-102282 A    4/2002
JP    2006-116348 A    5/2006
(Continued)

*Primary Examiner* — Catharine L Anderson
(74) *Attorney, Agent, or Firm* — Muncy, Geissler, Olds & Lowe, P.C.

(57) ABSTRACT

The present invention is intended to provide the advantages of forming the leg gathers with the liquid impervious film that allow reduction of the used amount of the non-woven fabric while suppressing the deterioration of the texture, and others. The foregoing issue is solved by providing leg gathers that have: an inside non-woven fabric layer constituting a width-direction inner surface; an outside non-woven fabric layer constituting a width-direction outer surface; elastically stretchable gather materials that are provided along the front-back direction between the inside non-woven fabric layer and the outside non-woven fabric layer of at least forward end portions in front-back direction intermediate portions; and a liquid impervious film that is sandwiched between the inside non-woven fabric layer and the outside non-woven fabric layer ranging from a base end to a position nearer a forward end side than the base end, and is configured such that parts of the leg gathers having the liquid impervious film nearer the base end side than the forward end portions constitute non-woven fabric absent (Continued)

parts where the inside non-woven fabric layer does not exist and the liquid impervious film is exposed.

5 Claims, 12 Drawing Sheets

(52) U.S. Cl.
CPC .................. *A61F 13/49453* (2013.01); *A61F 2013/49092* (2013.01)

(58) Field of Classification Search
CPC .. A61F 2013/49093; A61F 2013/49433; A61F 2013/4944; A61F 2013/4948; A61F 2013/49493; A61F 13/49446; A61F 13/49453

See application file for complete search history.

(56) References Cited

U.S. PATENT DOCUMENTS

| | | |
|---|---|---|
| 2002/0087139 A1 | 7/2002 | Popp et al. |
| 2013/0030402 A1 | 1/2013 | Arayama et al. |

FOREIGN PATENT DOCUMENTS

| | | |
|---|---|---|
| JP | 2008-295838 A | 12/2008 |
| JP | 2009-082358 A | 4/2009 |
| JP | 2013-252323 A | 12/2013 |
| JP | 2013-255849 A | 12/2013 |
| WO | WO2014/122980 A1 | 8/2014 |

* cited by examiner

UNDERPANTS-TYPE DISPOSABLE DIAPER

TECHNICAL FIELD

The present invention relates to an underpants-type disposable diaper with leg gathers on width-direction both sides of an absorption surface of an inner body.

BACKGROUND ART

In general, an underpants-type disposable diaper includes: an outer body forming individually or integrally a front body and a back body; an inner body that has an absorber and is attached to the inner surface of the outer body from the front body to the back body; and the outer body of the front body and the outer body of the back body are joined together at the both side edges to form a waist opening and a pair of right and left leg openings. The underpants-type disposable diaper also generally has leg gathers as parts standing toward the legs of a wearer on width-direction both sides of an absorption surface of the inner body to improve the fit to the legs and prevent lateral leakage (for example, see Patent Documents 1 to 3).

There have been generally proposed leg gathers with various structures. In a currently general structure, the leg gathers have attachment parts that are fixed to the back side of the inner body, extension parts that are extended from the attachment parts to surfaces of side parts of the inner body so as to wrap around lateral sides of the inner body, fallen parts that are formed by fixing front-back both end portions of the extension parts in a fallen state to the surfaces of the side parts of the absorbent article, free parts that are formed by not fixing intermediate portions of the fallen parts in the extension parts, and elastically stretchable gather materials that are fixed in an extended state along a front-back direction to at least forward end portions of the free parts. When the diaper is worn, the leg gathers stand by the contraction of the elastically stretchable gather materials at the free parts to form leakage prevention walls that fit elastically along the legs of the wearer.

The leg gathers are intended to prevent leakage. Therefore, the leg gathers desirably have sufficient water-shielding performance. In addition, the leg gathers are to contact with the wearer's skin and desirably have cloth-like texture. Accordingly, the leg gathers are generally structured to be entirely covered with water-repellent non-woven fabric with favorable texture. In addition, to provide water-shielding performance, a liquid impervious film is contained in the gathers or three-dimensional gathers are provided in a plurality of rows without the liquid impervious film.

Meanwhile, absorbent articles are to thrown away after use, and the control of material costs is one of very important issues. Conventionally, much effort has been devoted to changing the kinds of materials and employing less wasteful (efficient) materials.

However, there is still room for improvement in reduction of the materials for leg gathers. Specifically, with importance placed on the water-shielding performance of the leg gathers as described above, the liquid impervious film needs to be contained in the gathers, but the liquid impervious film is less preferable in texture. Therefore, it is considered that the front and back surfaces of the liquid impervious film need to be entirely covered with non-woven fabric in order to ensure the compatibility between water-shielding performance and favorable texture, and there is no room for improvement in the reduction of materials.

CITATION LIST

Patent Documents

Patent Document 1: Japanese Unexamined Patent Application Publication No. 2013-255849
Patent Document 2: Japanese Unexamined Patent Application Publication No. 2002-102282
Patent Document 3: Japanese Unexamined Patent Application Publication No. 2009-082358

SUMMARY OF INVENTION

Technical Problem

A major object of the present invention is to form leg gathers containing liquid impervious film in such a manner as to reduce the used amount of non-woven fabric while suppressing deterioration of texture.

Solution to Problem

The present invention having solved the foregoing problem is as follows:

An underpants-type disposable diaper, comprising: an outer body that forms individually or integrally a front body and a back body;

an inner body that has an absorber and is attached to the inner surface of the outer body from the front body through a crotch portion to the back body; and leg gathers as parts standing toward the legs of a wearer and extended along width-direction both sides of an absorption surface of the inner body, the outer body of the front body and the outer body of the back body being joined together at the both sides to form a waist opening and a pair of right and left leg openings, wherein the leg gathers have: an inside non-woven fabric layer constituting a width-direction inner surface; an outside non-woven fabric layer constituting a width-direction outer surface; elastically stretchable gather members that are provided along the front-back direction between the inside non-woven fabric layer and the outside non-woven fabric layer of at least forward end portions of the leg gathers in front-back direction intermediate portions of the leg gathers; and a liquid impervious film that is sandwiched between the inside non-woven fabric layer and the outside non-woven fabric layer ranging from base end-side to forward end-side positions, and parts of the leg gathers having the liquid impervious film and being nearer the base end side than the forward end portions constitute non-woven fabric absent parts where the inside non-woven fabric layer does not exist and the liquid impervious film is exposed.

(Operation and Effect)

The present invention makes it possible to reduce the used amount of the non-woven fabric by forming the non-woven fabric absent parts in the leg gathers without the inside non-woven fabric layer (the inside non-woven fabric layer is not provided). In addition, since the forward end portions of the leg gathers are brought into contact with the skin, providing the non-woven fabric absent parts on the base end side avoiding the forward end portions makes the liquid impervious film less prone to contact the skin, thereby suppressing the deterioration of texture.

Meanwhile, providing the liquid impervious film in the leg gathers makes it possible to prevent oozing of body fluid from the inner surface side to outer surface side of the leg gathers. In addition, forming the non-woven fabric absent parts in such a manner as to make the inside non-woven fabric layer intermittent, thereby to prevent propagation and diffusion of body fluid from the inner body side to the forward end side.

The underpants-type disposable diaper, wherein a plurality of elastically stretchable gather members are provided at intervals in a direction from the forward ends to the base ends, and the non-woven fabric absent parts are formed only between the elastically stretchable gather members.
(Operation and Effect)

The leg gathers as the parts standing toward the legs of the wearer are intended to prevent leakage of excretion to the outside. When a plurality of elastically stretchable gather materials is provided at intervals in the leg gathers, the portions of the leg gathers between the elastically stretchable gather materials are recessed toward the outside. Accordingly, when the non-woven fabric absent parts are provided only at the recessed portions, the liquid impervious film exposed to the non-woven fabric absent parts are recessed and less prone to contact the skin. In addition, the recessed portions act in such a manner that the liquid impervious film is less prone to contact the skin, and exert the effect of preventing the movement of the excretion toward the forward end side along the inner surfaces of the leg gathers. This enhances the effect of excretion leakage prevention.

The underpants-type disposable diaper, wherein the outer body includes separately a front-side outer body constituting the front body and a back-side outer body constituting the back body, the front-side outer body and the back-side outer body being not continuous but separated from each other at a crotch portion side, the leg gathers extend from a fixed section of the inner body with respect to the front-side outer body to a fixed section of the inner body with respect to the back-side outer body, and the leg gathers are extended to lateral sides of the inner body, front end portions of the leg gathers are set as fixation portions fixed to an inner surface of the front-side outer body and back end portions of the leg gathers are set as fixation portions fixed to an inner surface of the back-side outer body, and these fixation portions are contracted in a width direction by resilient and elastic members provided in the front-side outer body and the back-side outer body.
(Operation and Effect)

Forming the outer body in a front-back divided manner and extending the leg gathers to the lateral sides of the inner body makes it possible to obtain a very simple structure. In that case, the parts of the leg gathers overlapping the front-side outer body and the back-side outer body are pressed against the skin by the front-side outer body and the back-side outer body, and therefore the liquid impervious film exposed to the non-woven fabric absent parts may also be pressed against the skin. However, by fixing the parts to the front-side outer body and the back-side outer body and contracting the parts in the width direction by the resilient and elastic members in the front-side outer body and the back-side outer body, the area of the liquid impervious film contacting the skin significantly decreases due to contraction wrinkles even though the liquid impervious film is exposed, thereby reducing the influence on the texture.

The underpants-type disposable, comprising:

a liquid pervious top sheet of non-woven fabric that is provided on a front surface side of the absorber and extended beyond width-direction both sides of the absorber; and a gather sheet of non-woven fabric that is provided on a back surface side of the inner body and extended beyond the top sheet on the width-direction both sides of the absorber, wherein the width-direction both end portions of the gather sheet are folded and forward ends of the folded portions are separated from a forward end of the top sheet, the liquid impervious film is provided at least from a portion between the folded portions of the gather sheet to a portion between the top sheet and the gather sheet, and the outside non-woven fabric layer is formed by the portion of the gather sheet other than the folded portions, the inside non-woven fabric layer is formed by the folded portions of the gather sheet and the portions of the top sheet extended on the lateral sides of the absorber, and the non-woven fabric absent parts are formed as separated area between the folded portions of the gather sheet and the separated portions of the top sheet.
(Operation and Effect)

By forming the inside non-woven fabric layer nearer the base end side than the non-woven fabric absent parts in the leg gathers from the top sheet and forming the other parts from the gather sheet, it is possible to provide the non-woven fabric absent parts without having to cut the materials and simplify the structure of the parts to facilitate the manufacture.

The underpants-type disposable diaper, wherein the liquid impervious film is extended from one leg gather through the back surface side of the absorber to the other leg gather.
(Operation and Effect)

Providing the liquid impervious film makes it possible to ensure integrally the water-shielding performance of the leg gathers and water-shielding performance of the back side of the absorber.

The underpants-type disposable diaper, wherein the leg gathers include: attachment parts that are fixed to the back side of the inner body; extension parts that are extended from the attachment parts to surfaces of side parts of the inner body so as to wrap around the lateral sides of the inner body; fallen parts that are formed by fixing front-back both end portions of the extension parts in a fallen state to the surfaces of the side parts of the inner body; free parts that are formed by not fixing intermediate portions of the fallen parts in the extension parts; and elastically stretchable gather members that are fixed in an extended state along a front-back direction to at least forward end portions of the free parts, and the non-woven fabric absent parts are formed only in the portions of the extended parts opposed to the surfaces of the side part of the inner body.
(Operation and Effect)

The leg gathers as described above are generally used in underpants-type disposable diapers. To provide the non-woven fabric absent parts of the present invention in the leg gathers, the non-woven fabric absent parts are preferably provided in only the portions of the extension parts opposed to the surfaces of the side parts of the inner body because the liquid impervious film exposed to the insides of the leg gathers becomes less prone to contact the skin.

Advantageous Effects of Invention

As described above, according to the present invention, it is possible to provide the advantages of forming the leg gathers containing the liquid impervious film that allow reduction of the used amount of the non-woven fabric while suppressing the deterioration of the texture, and others.

DESCRIPTION OF EMBODIMENT

Figure 1:
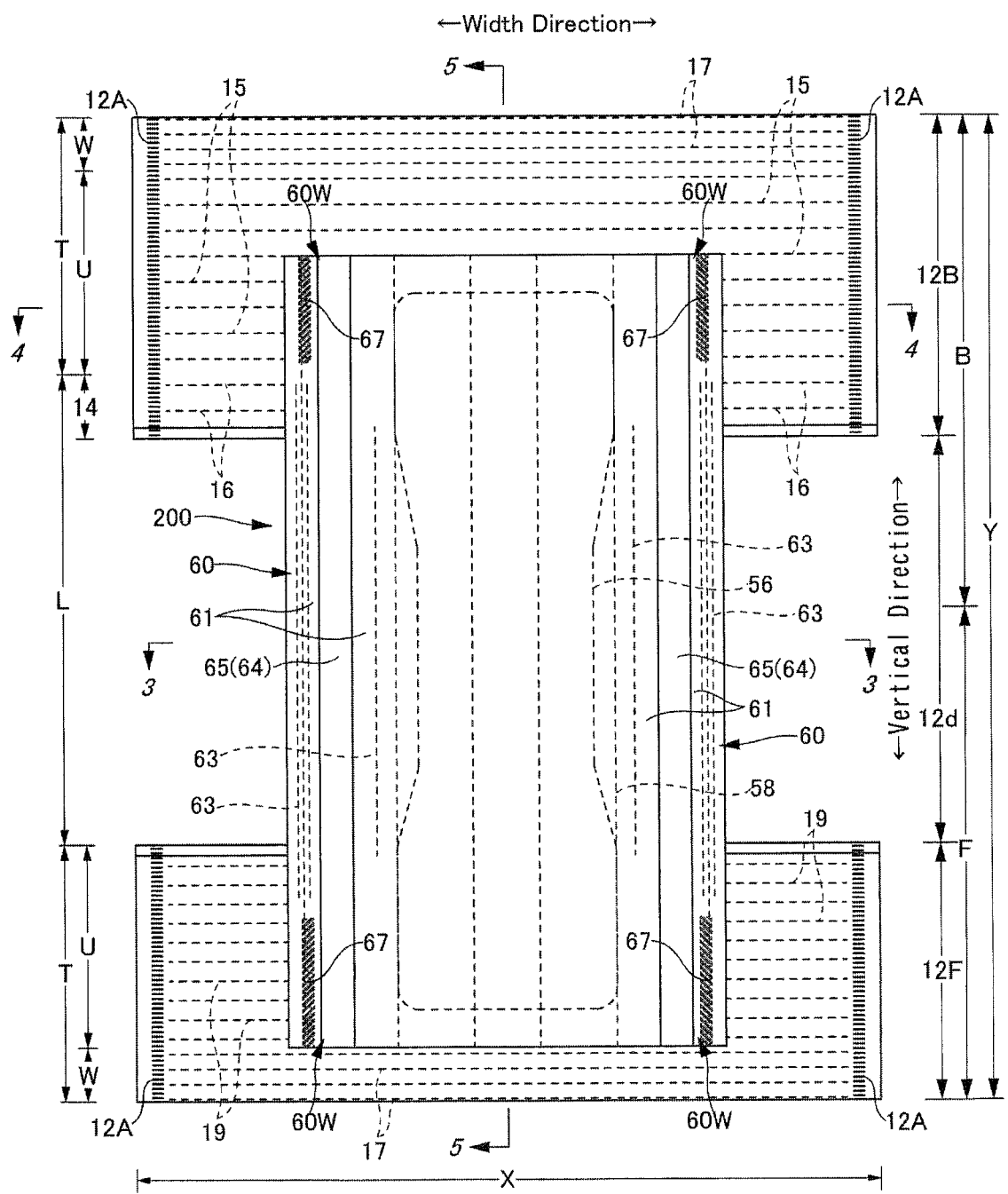
FIG. 1 is a plane view of an inner surface of an underpants-type disposable diaper in an unfolded state.
Figure 2:
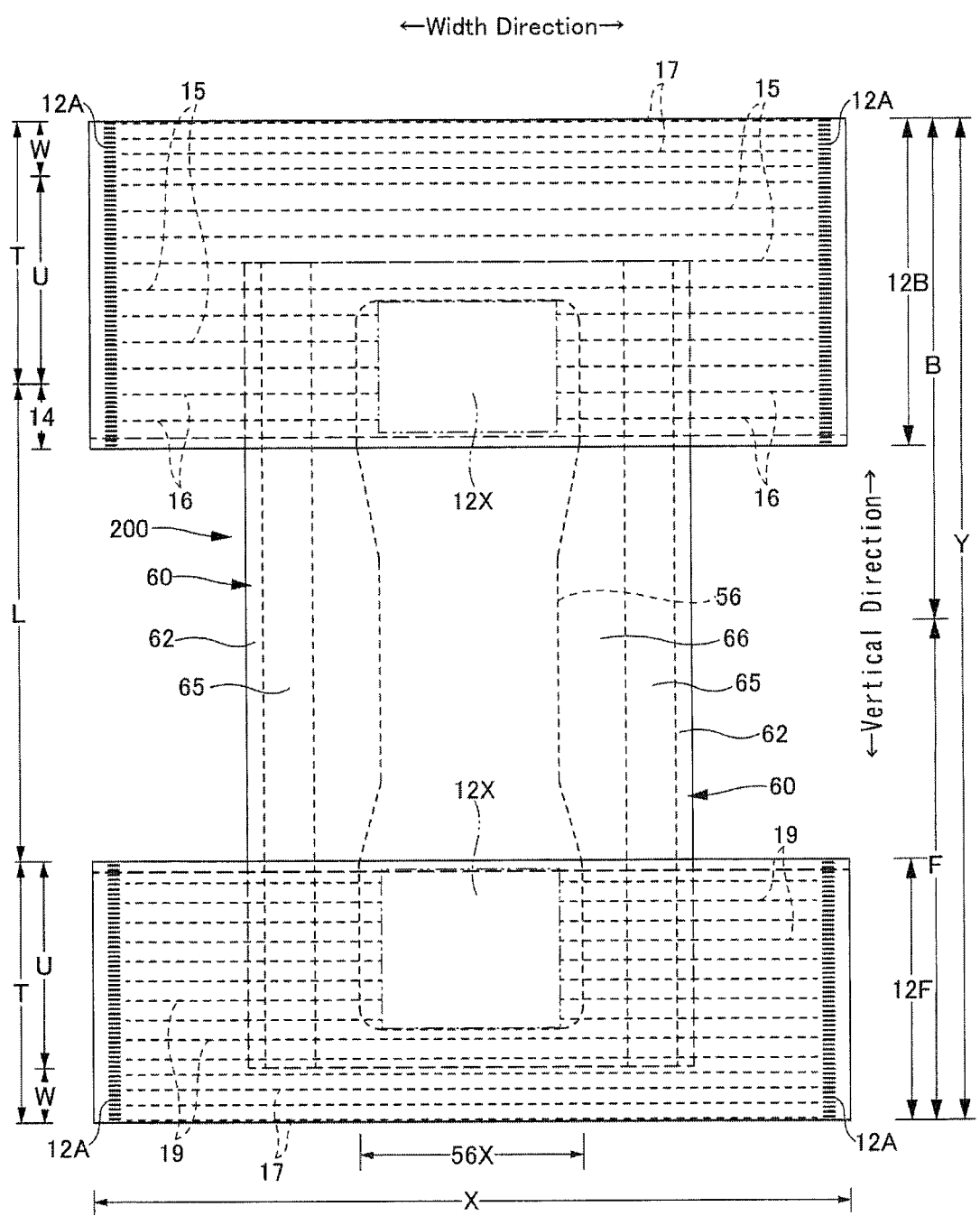
FIG. 2 is a plane view of an outer surface of the underpants-type disposable diaper in the unfolded state.

An embodiment of the present invention will be described below in detail with reference to the accompanying drawings.

FIGS. 1 to 7 illustrate an example of pants-type disposable diaper. The dot patterns in the cross-sectional views represent an adhesive as a joining means for joining the constituent members, which are located on front surface and back surface of the diaper. The hot-melt adhesive may be applied in a solid, bead, curtain, summit, or spiral pattern as the adhesive. Instead of or in addition to this, resilient and elastic members are fixed by applying the hot-melt adhesive to the outer peripheral surfaces of the resilient and elastic members with the use of a comb gun or a Sure-Wrap application means. The joining means for joining the constituent members may be a fixing means by material welding such as heat sealing or ultrasonic sealing.

The underpants-type disposable diaper 100 of the present embodiment includes outer bodies 12F and 12B that constitute a front body F and a back body B and an inner body 200 that is provided on the inside of the outer bodies 12F and 12B so as to extend from the front body F through a crotch portion to the back body B. The outer body 12F of the front body F and the outer body 12B of the back body B are joined together at the both sides to form side seal portions 12A. Reference sign Y represents the entire length of the diaper in an unfolded state (from the edge of a waist opening WO of the front body F to the edge of a waist opening WO of the back body B), and reference sign X represents the entire width of the diaper in the unfolded state.

The inner body 200 is a part absorbing and holding excrement such as urine, and an outer body 12 is a part for supporting the inner body 200 on the wearer's body. In the present embodiment, the upper opening of the outer bodies 12F and 12B constitutes the waist opening WO through which the wearer's waist is passed, and the parts of the inner body 200 surrounded by lower edges of the outer bodies 12F and 12B and side edges of the inner body 200 constitute the leg openings LO through which the wearer's legs are passed.

The underpants-type disposable diaper 100 of the present embodiment has a waist area T defined as a vertical zone with the side seal portions 12A (from the waist opening WO to the upper ends of the leg openings LO) and an intermediate area L defined as a front-back zone forming the leg openings LO (between the vertical zone with the side seal portions 12A of the front body F and the vertical zone with the side seal portions 12A of the back body B). The waist area T can be conceptually divided into a waist portion W forming the edge of the waist opening and a waist lower portion U as a portion under the waist portion W. In general, when the waist area T has boundaries between changes in the width-direction expansion and contraction stress (for example, the thickness or stretch rate of the resilient and elastic members changes), the side closer to the waist opening WO than the boundary closest to the waist opening WO constitutes the waist portion W. When the waist area T has no boundaries, the side closer to the waist opening WO than an absorber 56 or the inner body 200 constitutes the waist portion W. The vertical lengths of these parts vary depending on the size of the product and can be decided as appropriate. As an example, however, the vertical length of the waist portion W may be 15 to 40 mm, and the vertical length of the waist lower portion U may be 65 to 120 mm. The both edges of the intermediate area L are narrowed in a U shape or a curved shape along the circumferences of the wearer's legs, and the wearer's legs are passed through the narrowed ends. As a result, the underpants-type disposable diaper has an almost hourglass shape as a whole in the unfolded state.

(Outer Bodies)

Figure 11:
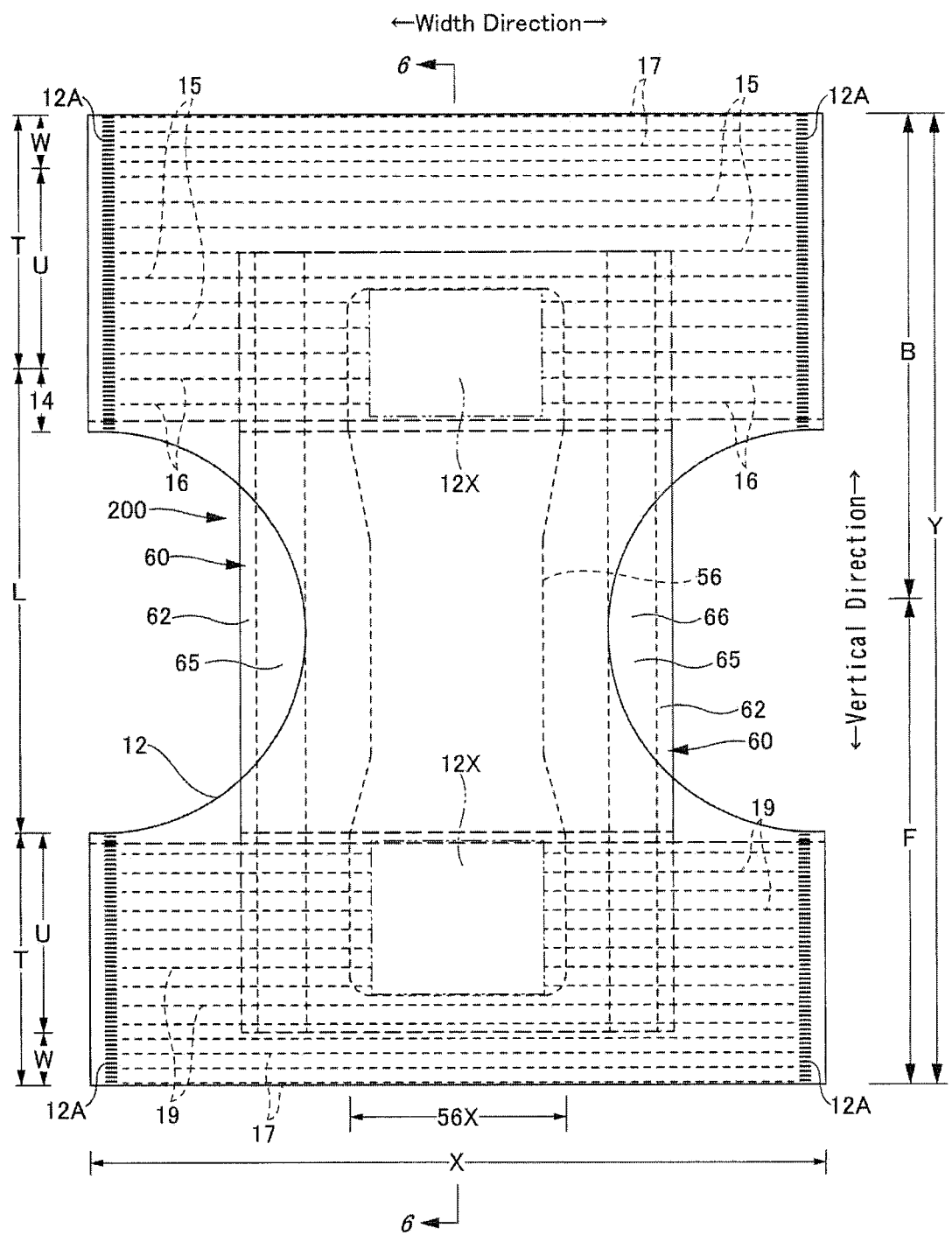
FIG. 11 is a planar view of the outer surface of an underpants-type disposable diaper in the unfolded state.
Figure 12:
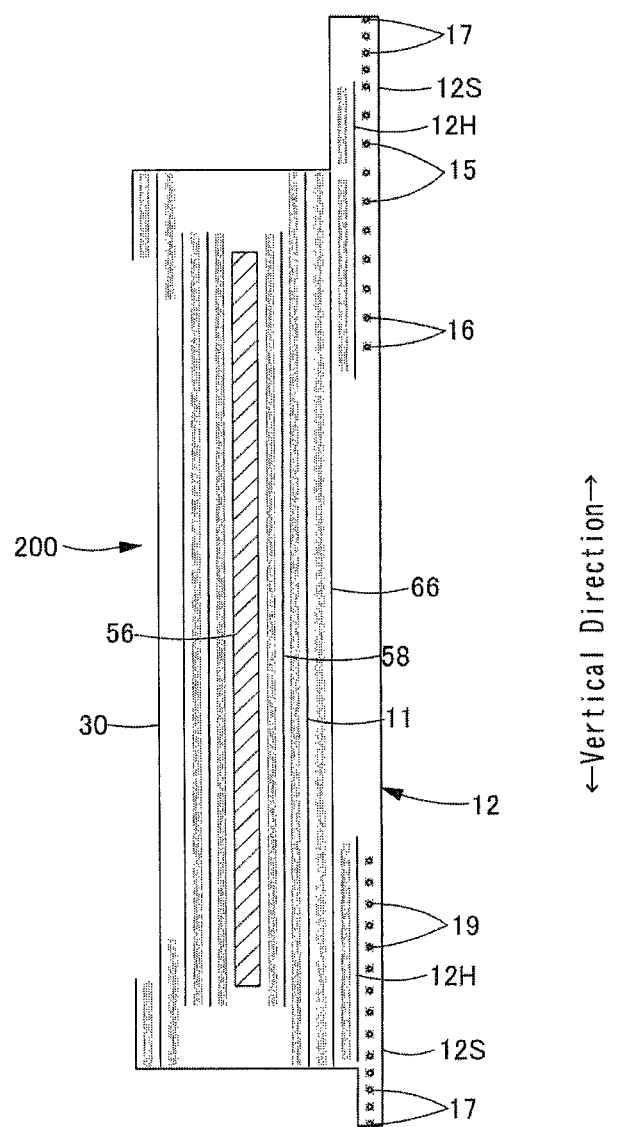
FIG. 12 is a cross-sectional view of FIG. 11 taken along line 6-6.

The outer bodies 12F and 12B include the front-side outer body 12F constituting the front body F and the back-side outer body 12B constituting the back body B, and the front-side outer body 12F and the back-side outer body 12B are not continuous but separated from each other on the leg sides. A distance 12d of separation can be about 150 to 250 mm. Although not illustrated, a crotch portion cover sheet made of non-woven fabric or the like may be stuck to cover partially the exposed portion of the back surface of the inner body 200 in the separated part (for example, the partially exposed portion ranges over the entire front-back exposed portion between the front-side outer body 12F and the back-side outer body 12B but does not extend up to the front and back ends of the inner body 200, and the width-direction both ends of the partially exposed portion also do not reach the both side edges of the inner body 200) or cover entirely the exposed portion of the same. In addition, the outer body 12 can be integrally formed to continue from the front body F through the crotch portion to the back body B as illustrated in FIGS. 11 and 12. That is, the outer bodies 12F and 12B individually constituting the front body F and the back body B in the present invention correspond to the former mode, and the outer body 12 integrally constituting the front body F and the back body B corresponds to the latter mode.

The outer bodies 12F and 12B have a waist part as a vertical zone corresponding to the first area T. In the present embodiment, the front-side outer body 12F has no part corresponding to the intermediate area L, but the back-side outer body 12B has a gluteal cover portion 14 that extends from the waist area T to the intermediate area L. Although not illustrated, the front-side outer body 12F may has a groin cover portion that extends from the waist area T to the intermediate area L or may have the groin cover portion but may not have the gluteal cover portion, or none of the front-side outer body 12F and the back-side outer body 12B may have a portion corresponding to the intermediate area L. In the illustrated mode, the lower edge of the gluteal cover portion 14 is linearly shaped along the width direction as with the lower edge of the front-side outer body 12F. Alternatively, the lower edge of the gluteal cover portion 14 may be formed in a curved shape so as to be positioned nearer the waist opening side with increasing proximity to the width-direction outside.

Figure 3:
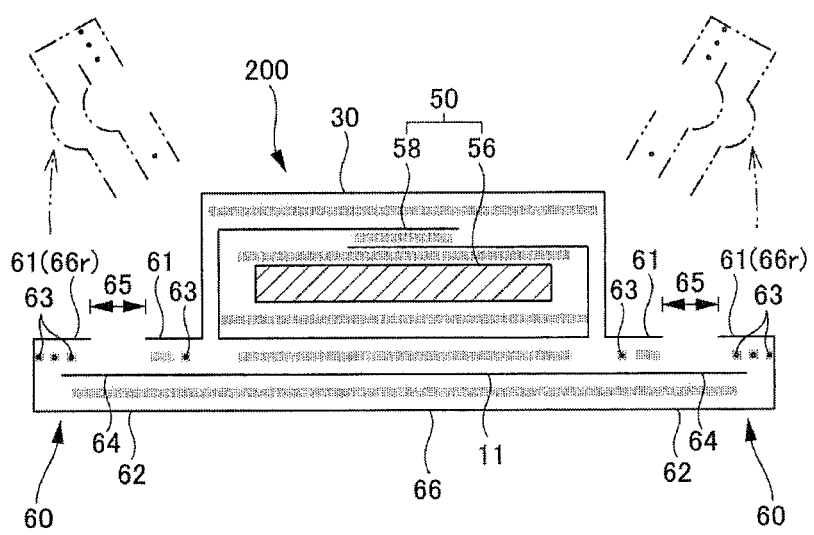
FIG. 3 is a cross-sectional view of FIG. 1 taken along line 3-3.
Figure 4:
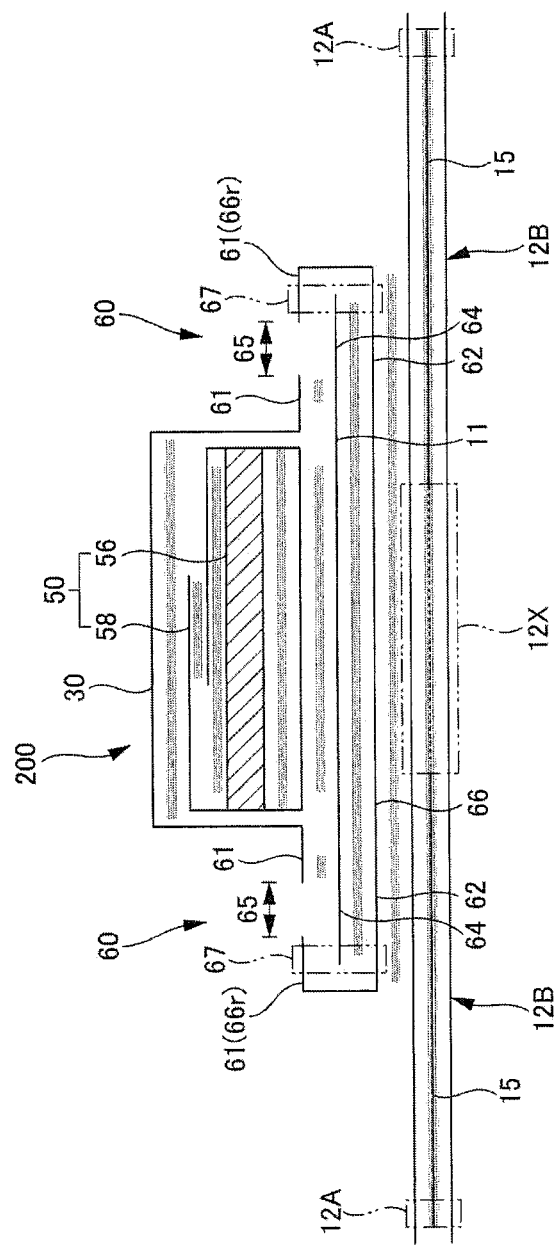
FIG. 4 is a cross-sectional view of FIG. 1 taken along line 4-4.
Figure 5:
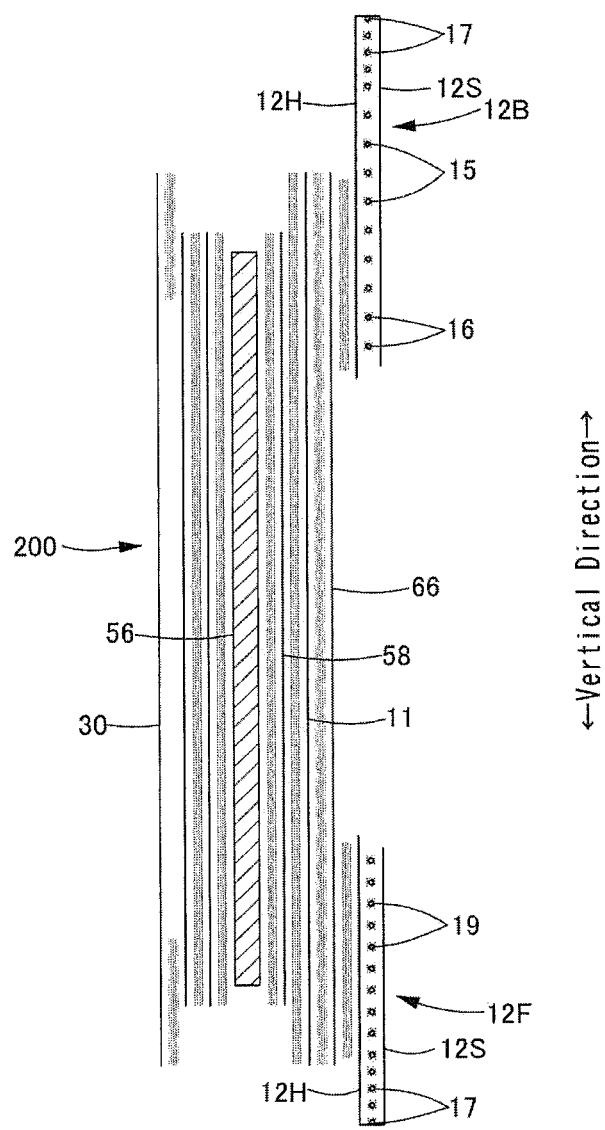
FIG. 5 is a cross-sectional view of FIG. 1 taken along line 5-5.

The outer bodies 12F and 12B are formed by joining an outside sheet layer 12S and an inside sheet layer 12H with a joining means such as a hot-melt adhesive or welding as illustrated in FIGS. 3 to 5. The outside sheet layer 12S and the inside sheet layer 12H may be formed by folding one sheet material with a crease on the waist opening side as illustrated in FIG. 5 or may be formed by sticking together two sheet materials as illustrated in FIG. 12.

There is no particular limitation on the sheet materials for the outside sheet layer 12S and the inside sheet layer 12H as far as they are sheet-like materials, but they are preferably formed from non-woven fabric. There is no particular limitation on raw fibers for the non-woven fabric. For example, the raw fibers may be synthetic fibers based on olefin such as polyethylene or polypropylene, or based on polyester or polyamide, or reproduced fibers of rayon or cupra, natural fibers of cotton or the like, mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. In the case of using non-woven fabric, its basis weight is preferably about 10 to 30 g/m$^2$.

In addition, the total basis weight of the outer bodies 12F and 12B is preferably about 20 to 60 g/m$^2$.

The outer bodies 12F and 12B have elongated resilient and elastic members 15 to 19 such as rubber threads provided at a predetermined stretch rate between the outside sheet layer 12S and the inside sheet layer 12H to enhance the fit to the wearer's waist. The elongated resilient and elastic members 15 to 19 may be formed from synthetic rubber or natural rubber. The outside sheet layer 12S and the inside sheet layer 12H in the outer bodies 12F and 12B can be bonded to each other and the elongated resilient and elastic members 15 to 19 sandwiched between the sheet layers 12S and 12H can be fixed by at least one of a hot-melt adhesive used in various application methods and a fixing means for material welding such as heat sealing or ultrasound sealing. Fixing firmly the entire outer bodies 12F and 12B is not preferable because this deteriorates the flexibility of the sheets. Accordingly, it is preferable that the parts other than the bonding parts of the elongated resilient and elastic members 15 to 19 are not bonded or are lightly bonded. In the illustrated mode, a hot-melt adhesive is applied only to the outer peripheral surfaces of the elongated resilient and elastic members 15 to 19 by an application means such as a comb gun or a sure-wrap nozzle and the elongated resilient and elastic members 15 to 19 are sandwiched between the two sheet layers 12S and 12H, whereby the elongated resilient and elastic members 15 to 19 can be fixed to the two sheet layers 12S and 12H and the two sheet layers 12S and 12H can be fixed to each other only by the hot-melt adhesive applied to the outer peripheral surfaces of the elongated resilient and elastic members 15 to 19.

More specifically, between the outer sheet layer 12S and the inner sheet layer 12H in the waist portions W of the outer bodies 12F and 12B, a plurality of waist portion resilient and elastic members 17 is fixed in a stretched state along the width direction at a predetermined stretch rate and at vertical intervals in such a manner as to be entirely continuous in the width direction. One or more of the waist portion resilient and elastic members 17 in the area adjacent to the waist lower portion U may overlap the inner body 200 or may be provided only on the width-direction both sides of the width-direction intermediate portion overlapping the inner body 200 excluding the width-direction intermediate portion. As the waist portion resilient and elastic members 17, about 3 to 22 rubber threads with a thickness of about 155 to 1880 dtex, in particular about 470 to 1240 dtex (this is applied to a synthetic rubber, and in the case of using a natural rubber, a cross-section area of about 0.05 to 1.5 mm$^2$, in particular about 0.1 to 1.0 mm$^2$) are preferably fixed at a stretch rate of about 150 to 400%, in particular about 220 to 320%, and at intervals of 4 to 12 mm. All of the waist portion resilient and elastic members 17 may not be equal in thickness and stretch rate. For example, the resilient and elastic members may be different in thickness and stretch rate between the upper and lower sides of the waist portions W.

In the waist lower portions U of the outer bodies 12F and 12B, a plurality of waist lower portion resilient and elastic members 15 and 19 composed of elongated resilient and elastic members is fixed in an extended state in the width direction at a predetermined stretch rate and at vertical intervals in such a manner as to be entirely continuous in the width direction, between the outer sheet layer 12S and the inner sheet layer 12H only on the upper side and width-direction both sides of the width-direction intermediate portion overlapping the inner body 200 excluding the width-direction intermediate portion.

As the waist lower portion resilient and elastic members 15 and 19, about 5 to 30 rubber threads with a thickness of 155 to 1880 dtex, in particular about 470 to 1240 dtex (this is applied to a synthetic rubber, and in the case of using a natural rubber, a cross-section area of about 0.05 to 1.5 mm$^2$, in particular about 0.1 to 1.0 mm$^2$) are preferably fixed at a stretch rate of about 200 to 350%, in particular about 240 to 300%, and at intervals of 1 to 15 mm, in particular 3 to 8 mm.

In the gluteal cover portion 14 of the back-side outer body 12B between the outside sheet layer 12S and the inside sheet layer 12H, a plurality of cover portion resilient and elastic members 16 formed from elongated resilient and elastic members is fixed in a stretched state along the width direction at a predetermined stretch rate and at vertical intervals in such a manner as to be entirely continuous in the width direction between the outer sheet layer 12S and the inner sheet l12H only on the width-direction both sides of the width-direction intermediate portion overlapping the inner body 200 excluding the width-direction intermediate portion.

As the cover portion resilient and elastic members 16, about two to ten rubber threads with a thickness of 155 to 1880 dtex, in particular about 470 to 1240 dtex (this is applied to a synthetic rubber, and in the case of using a natural rubber, a cross-section area of 0.05 to 1.5 mm$^2$, in particular about 0.1 to 1.0 mm$^2$) are preferably fixed at a stretch rate of about 150 to 300%, in particular about 180 to 260%, and at intervals of 5 to 40 mm, in particular 5 to 20 mm.

In the case of providing the groin cover portion to the front-side outer body 12F, cover portion resilient and elastic members can be similarly provided.

When the waist lower portion resilient and elastic members 15 and 19 and the cover portion resilient and elastic members 16 are provided only on the width-direction both sides of the partial or entire width-direction intermediate portion overlapping the inner body 200 as illustrated in the drawings, the inner body 200 does not contract more than necessary in the width direction, or become fluffy with deterioration in appearance, or decrease in absorbing performance. This mode includes the mode in which the resilient and elastic members exist only on the width-direction both sides, and the mode in which the resilient and elastic members exist crossing over the inner body 200 from one to the other sides in the width direction, but the resilient and elastic members are finely cut to exert no contraction force on the width-direction intermediate portions of the portion overlapping the inner body 200 or the entire portion overlapping the inner body 200 (this substantially means that no resilient and elastic members are provided) as illustrated with reference sign 12X in FIGS. 2 and 4, and thus the contraction force of the resilient and elastic members acts only on the width-direction both sides. As a matter of course, the disposed modes of the waist lower portion resilient and elastic members 15 and 19 and the cover portion resilient and elastic members 16 are not limited to the foregoing ones. Alternatively, some or all of the waist lower portion resilient and elastic members 15 and 19 and the cover portion resilient and elastic members 16 may be provided crossing over the inner body 200 from the one to the other sides in the width direction so that the contraction force acts entirely in the width direction including the portion overlapping the inner body 200.

(Inner Body)

The inner body 200 have an arbitrary shape but is rectangular in the illustrated example. As illustrated in FIGS. 3 to 5, the inner body 200 is a liquid pervious top sheet 30 on the wearer's skin side, a liquid impervious film 11, and an absorbent element 50 interposed between the top sheet 30 and the liquid impervious film 11. Reference sign 40 represents an intermediate sheet (second sheet) that is interposed between the top sheet 30 and the absorbent element 50 to move liquid having passed through the top sheet 30 quickly to the absorbent element 50. Reference sign 60 represents leg gathers 60 that are extended on the width-direction both sides of the absorption surface of the inner body and stand toward the wearer's legs to prevent leakage of excretion to the both sides of the inner body 200.

(Top Sheet)

The top sheet 30 may be formed from porous or non-porous non-woven fabric or a porous plastic sheet with no particular limitation as far as it is made of a liquid pervious material. In the case where the top sheet 30 also acts as the cover material for a liquid impervious film 64 of the leg gathers 60 as illustrated in the modes of FIGS. 3 and 4, non-woven fabric is used. There is no particular limitation on raw fibers for the non-woven fabric. For example, the raw fibers may be synthetic fibers based on olefin such as polyethylene or polypropylene, or based on polyester or polyamide, or reproduced fibers of rayon or cupra, natural fibers of cotton or the like, mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle punching, air-through processing, and point bonding. For flexibility and drape properties, spun-bonding and spun-lacing methods are preferred. For bulkiness and softness, air-through processing, point-bonding, and thermal bonding methods are preferred.

The top sheet 30 may be composed of a single sheet or a layered sheet obtained by sticking two or more sheets each other. Similarly, the top sheet 30 may be composed of a single sheet or two or more sheets in a planar direction.

Figure 8:
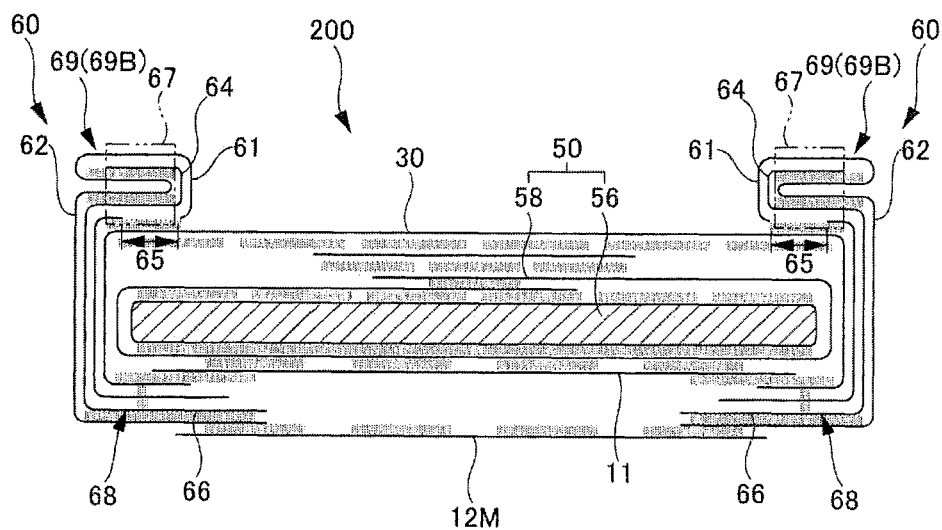
FIG. 8 is a cross-sectional view of an inner body that corresponds to the cross-sectional view taken along line 4-4 illustrated in FIG. 1.
Figure 9:
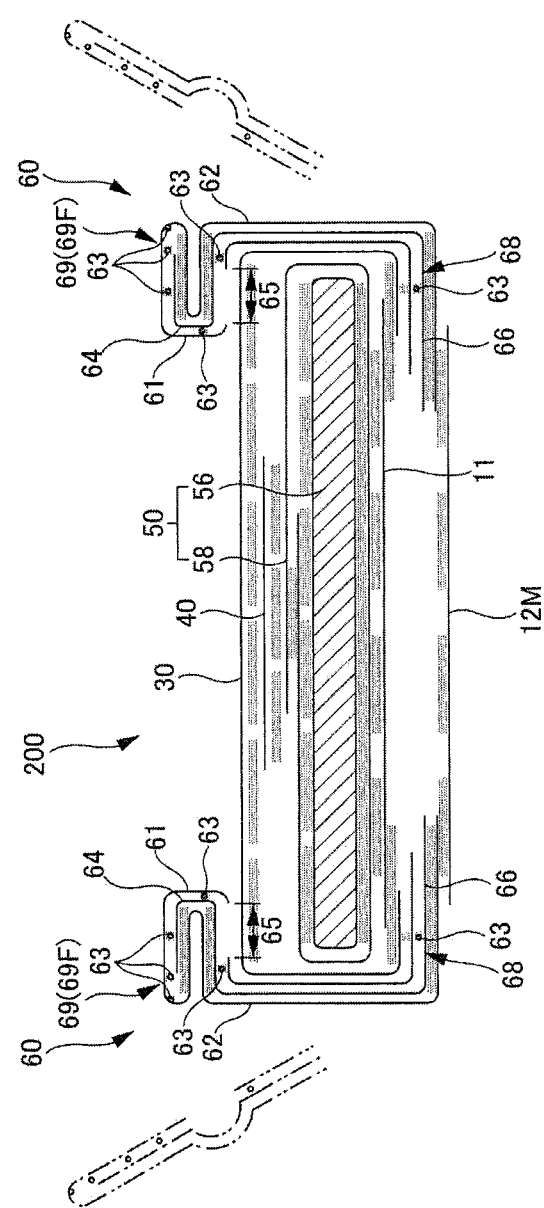
FIG. 9 is a cross-sectional view that corresponds to the cross-section taken along line 3-3 illustrated in FIG. 1.

In the case where the width-direction both sides of the top sheet 30 do not act as the covering material for the liquid impervious film 64 of the leg gathers 60, for example, as in the mode illustrated in FIGS. 8 and 9, the top sheet 30 can be extended up to the back side of the absorbent element 50 through the space between the absorbent element 50 and the leg gathers 60, and can be bonded to the liquid impervious film 11 and the leg gathers 60 by a hot-melt adhesive or the like to prevent liquid penetration.

(Intermediate Sheet)

As in the mode illustrated in FIGS. 8 and 9, the intermediate sheet (called also "second sheet") 40 higher in hydrophilic property than the top sheet 30 may be provided on the back side of the top sheet 30. The intermediate sheet 40 prevents a reflowing phenomenon of the absorbed liquid from the absorber to keep the top sheet 30 in a dry texture. The intermediate sheet 40 may not be provided.

The material for the interlayer sheet 40 may be the same material as that for the top sheet 30, a spun-laced, spun-bonded, SMS, or pulp non-woven fabric sheet, a sheet of mixture of pulp and rayon, point-bonded paper, or crepe paper, for example. In particular, the air-through non-woven fabric is preferred for its bulkiness. Core-sheath composite fibers are preferably used for the air-through non-woven fabric. The resin for use in the core may be polypropylene (PP) but is preferably polyester (PET) for its high rigidity. The basis weight is preferably 20 to 80 $g/m^2$, more preferably 25 to 60 $g/m^2$. The thickness of the raw fibers in the non-woven fabric is preferably 2.2 to 10 dtex. To make the non-woven fabric high in bulkiness, eccentric fibers with no core in the center, hollow fibers, or eccentric and hollow fibers are preferably used for some or all of the raw fibers.

In the illustrated mode, the interlayer sheet 40 is shorter than the width of an absorber 56 and arranged in the center of the absorber 56. Alternatively, the interlayer sheet 40 may be provided over the entire width of the absorber 56. The longitudinal length of the interlayer sheet 40 may be the same as the length of the absorber 56 or may fall within a shorter-length range centered on the area for receiving the liquid.

(Liquid Impervious Film)

There is no particular limitation on the material for the liquid impervious film 11 provided on the back surface of the absorber 56. For example, the liquid impervious film 11 may be formed from a plastic film made of an olefin resin such as polyethylene or polypropylene. The liquid impervious film 11 is preferably formed from a liquid impervious and moisture-pervious material having been used preferably in recent years from the viewpoint of stuffiness prevention. As the moisture-pervious plastic film, there has been widely used a microporous plastic film that is obtained by melting and kneading an inorganic filling agent in an olefin resin such as polyethylene or polypropylene to form a sheet and then elongating the sheet in a uniaxial or biaxial direction.

The liquid impervious film 11 may be extended to the lateral side more than the absorber 56 as in the mode illustrated in FIGS. 3 and 4 to act also as the liquid pervious film 64 in the leg gathers 60, or may have a width falling within the back side of the absorbent element 50, or may wrap around the width-direction both sides of the absorbent element 50 to extend up to the both sides of the absorbent element 50 on the side parts of the top sheet 30 as in the mode illustrated in FIGS. 8 and 9.

An excretion indicator changed in color by absorption of a liquid may be provided on the inside of the liquid impervious film 11, in particular, on the side surfaces of the absorber 56.

(Absorbent Element)

The absorbent element 50 has the absorber 56 and a wrapping sheet 58 for wrapping the entire absorber 56. The wrapping sheet 58 may not be provided.

(Absorber)

The absorber 56 can be formed from a fiber assembly. The fiber assembly may be accumulated short fibers such as fluff pulp or synthetic fibers or a filament assembly obtained by opening tows (fiber bundles) of synthetic fibers such as cellulose acetate as necessary. The basis weight of the fluffy pulp or accumulated short fibers may be about 100 to 300 g/m$^2$, and the basis weight of the filament assembly may be about 30 to 120 g/m$^2$, for example. The fineness of synthetic fibers is 1 to 16 dtex, preferably 1 to 10 dtex, more preferably 1 to 5 dtex, for example. In the case of the filament assembly, the filaments may be non-crimped fibers but are preferably crimped fibers. The number of crimps in the crimped fibers may be about 5 to 75 per inch, preferably 10 to 50 per inch, more preferably about 15 to 50 per inch, for example. The crimped fibers are evenly crimped in many cases. High-absorbent polymer particles are preferably dispersed and held in the absorber 56.

Figure 6:
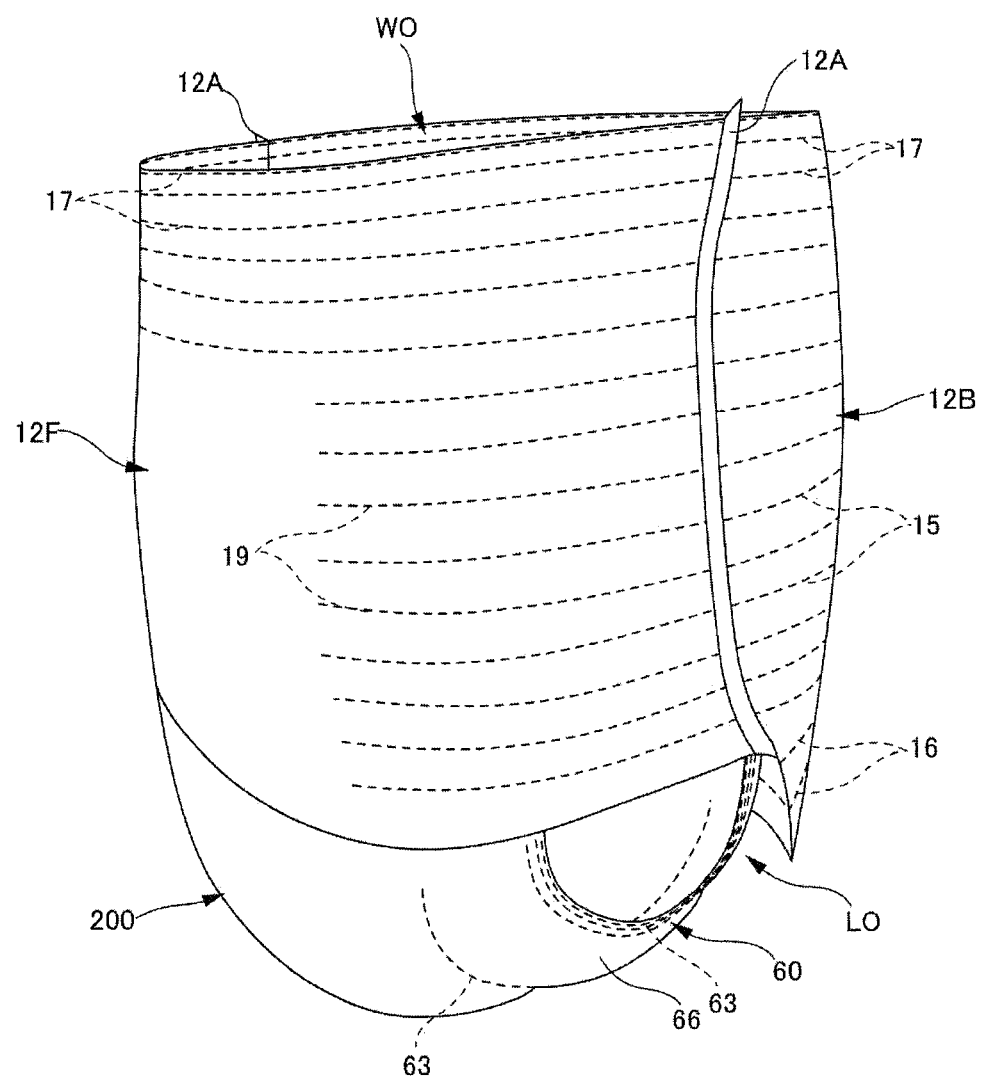
FIG. 6 is a perspective view of the underpants-type disposable diaper.

The absorber 56 may be rectangular in shape but preferably has an hourglass shape with a front end portion, a back end portion, and a narrower portion that is positioned between the front and back end portions and is narrower than the two end portions as illustrated in FIG. 6 to improve the fit of the absorber 56 and the leg gathers 60 to the circumferences of the legs.

The dimensions of the absorber can be decided as appropriate. Nevertheless, the absorber preferably extends to the peripheral edges or their neighborhoods of the inner body in the front-back direction and the width direction. Reference sign 56X represents the width of the absorber 56.

(High-Absorbent Polymer Particles)

The absorber 56 may partially or entirely contain high-absorbent polymer particles. The high-absorbent polymer particles include "powder" as well as "particles". The high-absorbent polymer particles 54 may be particles to be generally used in this type of absorbent article. For example, when being screened by the use of a standard 500-μm screen (JIS Z8801-1: 2006) (5-minute shaking), the ratio of the particles left on the screen is desirably 30 weight % or less, and when being screened by the use of a standard 180-μm screen (JIS Z8801-1: 2006) (5-minute shaking), the ratio of the particles left on the screen is desirably 60 weight % or more.

There is no particular limitation on the material for the high-absorbent polymer particles but the material preferably has a water absorption capacity (JIS K7223-1996 "Testing method for water absorption capacity of super absorbent polymers") of 40 g/g or more. The high-absorbent polymer particles may be based on starch, cellulose, or synthetic polymer. The high-absorbent polymer particles may be made of a starch-acrylate graft copolymer, a saponified substance of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 70 seconds or less, in particular 40 seconds or less. At too low a water absorption rate, the absorbed liquid is more likely to flow back from the absorber 56 to the outside.

The gel strength of the high-absorbent polymer particles is preferably 1000 Pa or more. Accordingly, it is possible to suppress effectively a sticky feeling of the absorber 56 after liquid absorption even when the absorber 56 is of high bulk.

The basis weight of the high-absorbent polymer particles can be decided as appropriate in the absorbing capability required for the use of the absorber 56. Although not definitely specified, the basis weight may be 50 to 350 g/m$^2$. When the basis weight of the polymer is less than 50 g/m$^2$, it is difficult to provide the necessary absorbing capability. When the basis weight of the polymer exceeds 350 g/m$^2$, the absorbing effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion area than the other areas. With regard to gender differences, the dispersing density (quantity) of the high-absorbent polymer particles may be increased at the front side of the product for male, and may be increased at the central portion of the product for female. In addition, the polymer may not be provided locally (in spots, for example) in the planar direction of the absorber 56.

(Wrapping Sheet)

The material for the wrapping sheet 58 may be the liquid impervious materials such as tissue paper, in particular, crepe paper, non-woven fabric, polyethylene-laminated non-woven fabric, a porous sheet, or the like. However, the material sheet is desirably configured to retain the high-absorbent polymer particles. In the case of using non-woven fabric instead of crepe paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of manufacture and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back end portions extended off from the front and back sides of the absorber 56 so that the extended portions are crushed on the top and bottom sides and joined together by a joining means such as a hot-melt adhesive.

(Leg Gathers)

The leg gathers 60 are parts that are extended along the width-direction both sides of the absorption surface of the inner body 200 and stand toward the wearer's legs. The leg gathers 60 are provided to shut off urine and loose stool moving in the lateral direction over the top sheet 30 and prevent lateral leakage.

As illustrated in FIGS. 3 and 4, the leg gathers 60 of the present embodiment have an inside non-woven fabric layer 61 constituting a width-direction inside surface, an outside non-woven fabric layer 62 constituting a width-direction outside surface, elastically stretchable gather materials 63 that are provided along the front-back direction between the inside non-woven fabric layer 61 and the outside non-woven fabric layer 62 at least in the forward ends of the front-back intermediate portions, and the liquid impervious film 64 (11) that is sandwiched between the inside non-woven fabric layer 61 and the outside non-woven fabric layer 62 ranging from the base end portions to the positions nearer the forward end portions than the base ends as illustrated in FIGS. 3 and 4. Characteristically, the parts of the leg gathers 60 having the liquid impervious film 64 and positioned nearer the base end side than the forward end portions are set as non-woven fabric absent parts 65 where the liquid impervious film 64 is exposed without the inside non-woven fabric layer 61 along the entire front-back sides of the leg gathers 60. Providing the leg gathers 60 with the non-woven fabric absent parts 65 without the inside non-woven fabric layer 61 makes it possible to reduce the used amount of non-woven fabric. In addition, since the forward end portions of the leg gathers 60 are brought into contact with the skin, and the non-woven fabric absent parts 65 are provided to the leg gathers 60 except the forward end portions, thereby to make the liquid impervious film 64 less prone to contact the skin and suppress the deterioration of the texture.

The elastically stretchable gather materials 63 may be provided only in the forward end portions of the leg gathers 60, but preferably, the plurality of elastically stretchable gather materials 63 is provided at intervals in the direction from the forward ends to the base ends of the leg gathers 60 as in the illustrated mode. In general cases, the number of the elastically stretchable gather materials 63 is preferably 2 to 6, and an interval 60d therebetween is preferably 3 to 10 mm. When the plurality of elastically stretchable gather materials 63 is provided at the intervals as described above, the interval portions are recessed to the outside. Accordingly, when the non-woven fabric absent parts 65 are provided only in the recessed portions as in the illustrated mode, the liquid impervious film 64 exposed to the non-woven fabric absent parts 65 is preferably recessed and less prone to contact the skin. In this case, more preferably, one or more elastically stretchable gather materials 63 are provided at intervals at least in the forward end portions and the base end portions of the leg gathers 60, and the non-woven fabric absent parts 65 are provided only in the interval portions between the elastically stretchable gather materials 63 in the base end portions and the elastically stretchable gather materials 63 in the forward end portions as in the mode illustrated in FIGS. 1 to 7.

The front-back zones in the elastically stretchable gather materials 63 provided in the leg gathers 60 may range over the entire front-back side of the leg gathers 60 but are preferably equal to or smaller than the front-back zones of the standing parts.

Figure 10:
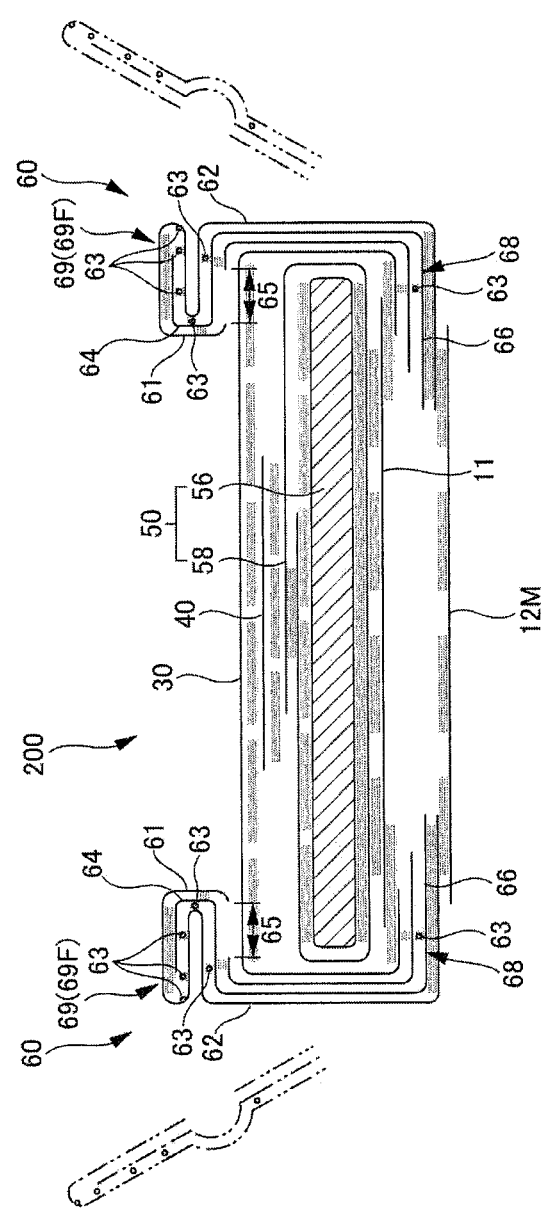
FIG. 10 is a cross-sectional view that corresponds to the cross-section taken along line 3-3 illustrated in FIG. 1.

The elastically stretchable gather materials 63 may be provided inside the liquid impervious films contained in the leg gathers as in the mode illustrated in FIGS. 3 and 9 or may be provided outside the liquid impervious films as in the mode illustrated in FIG. 10 as far as they are provided between the inside non-woven fabric layer 61 and the outside non-woven fabric layer 62 (accordingly, the elastically stretchable gather materials 63 are not provided in the non-woven fabric absent parts 65).

The liquid impervious film 64 may be provided from the base ends to the intermediate positions between the base ends and the forward ends of the leg gathers 60 as far as it falls within the range from the base ends to the positions nearer the forward end sides than the base ends of the leg gathers 60. However, the liquid impervious film 64 is preferably provided up to the forward end portions of the leg gathers 60 to improve sufficiently the water-shielding performance. More preferably, the liquid impervious film 64 is provided up to the positions slightly separated from the forward end portions (for example, the separation corresponds to a number of elastically stretchable gather materials, specifically, about 5 to 30 mm) as in the mode illustrated in FIGS. 3 and 4, and the liquid impervious film 64 is not contained in the forward end portions of the leg gathers 60 to maintain texture and flexibility.

Figure 7:
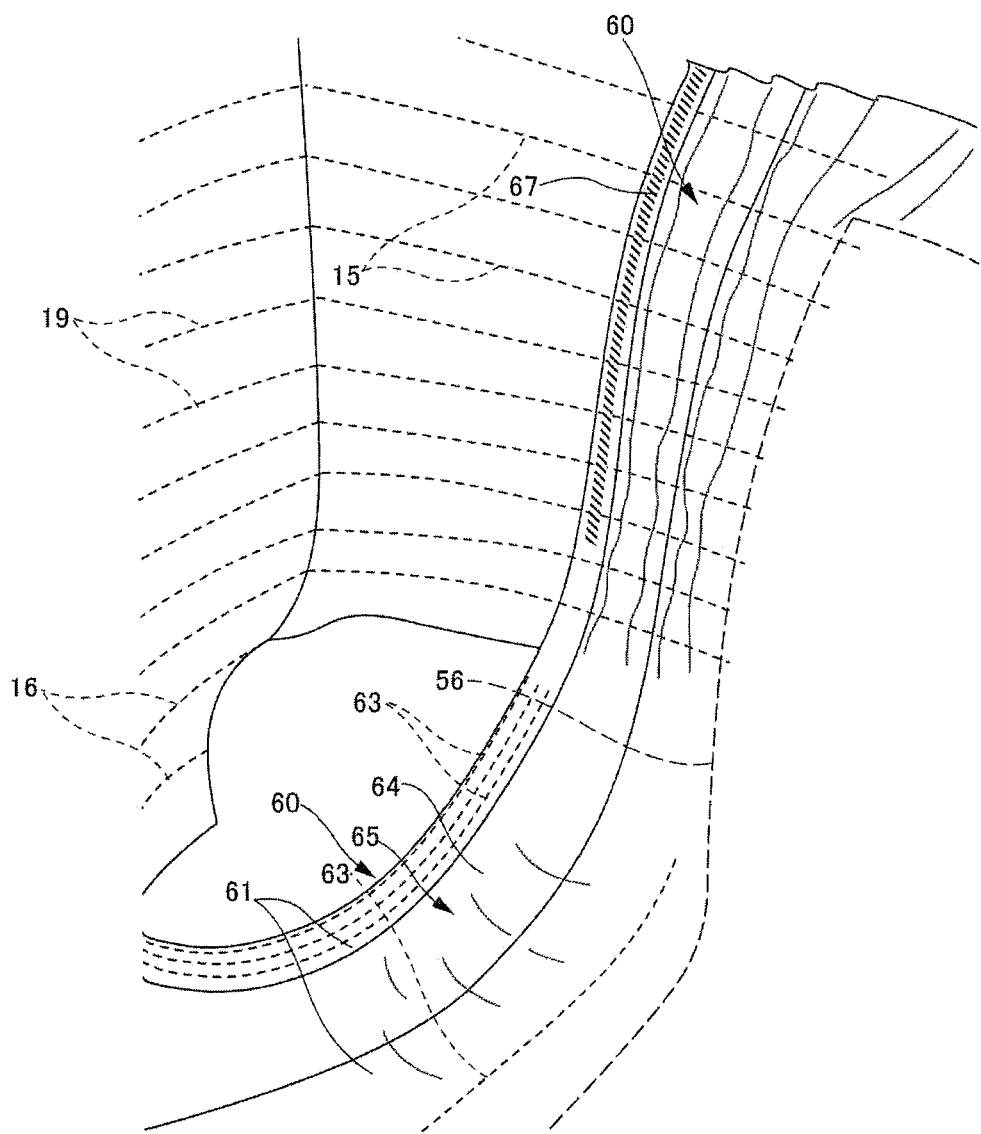
FIG. 7 is a perspective view of main components of inner left side of the underpants-type disposable diaper.

In the mode illustrated in FIGS. 1 to 7, the outer body is divided into the front and the back parts to simplify the structure, and the leg gathers 60 are extended to the lateral sides of the inner body 200 without folding (or the leg gathers 60 may be folded like an accordion). In that case, parts 60W of the leg gathers 60 overlapping the front-side outer body 12F and the back-side outer body 12B are pressed against the skin by the front-side outer body 12F and the back-side outer body 12B. Accordingly, the liquid impervious film 64 in the parts 60W exposed to the non-woven fabric absent parts 65 may be pressed against the skin. However, by fixing the parts 60W to the front-side outer body 12F and the back-side outer body 12B and contracting the parts 60W in the width direction by the resilient and elastic members 15 and 19 in the front-side outer body 12F and the back-side outer body 12B as in the mode illustrated in FIGS. 1 to 7, the areas of the parts 60W in contact with the skin are significantly reduced due to contraction wrinkles as illustrated in FIG. 7 even though the liquid impervious film 64 is exposed, thereby exerting less influence on the texture. In this mode, the regions between the fixation parts 60W of the leg gathers 60 to the front-side outer body 12F and the back-side outer body 12B stand toward the legs as shown by two-dot chain lines in FIG. 3 from the side edges of the absorber 56 as base ends due to the contraction of the elastically stretchable gather materials 63.

There is no particular limitation on the components of the leg gathers 60 but the leg gathers 60 can have any publicly known structure. In the mode illustrated in FIGS. 1 to 7, the top sheet 30 is made of non-woven fabric and is configured to have the width-direction both sides extending beyond the side edges of the absorber 56. In addition, a gather sheet 66 made of non-woven fabric is provided on the back side of the absorber 56 and is configured to have the both-side both sides extending beyond the side edges of the absorber 56. Further, the side edge portions of the gather sheet 66 are folded and the forward ends of the folded portions 66r are separated from the forward end of the top sheet 30, and the liquid impervious film 64 is provided at least ranging from the position between the folded portions 66r of the gather sheet 66 to the position between the top sheet 30 and the gather sheet 66. As a result, the outside non-woven fabric layer 62 is formed by the portion of the gather sheet 66 other than the folded portions 66r, the inside non-woven fabric layer 61 is formed by the folded portions 66r of the gather sheet 66 and the portions of the top sheet 30 extending beyond the lateral sides of the absorber 56, and the non-woven fabric absent parts 65 are formed by the portions between the folded portions 66r of the gather sheet 66 and the top sheet 30. By forming the inside non-woven fabric layer 61 of the leg gathers 60 nearer then base end side than the non-woven fabric absent parts 65 from the top sheet 30 and forming the other portions from the gather sheet 66, it is possible to provide the non-woven fabric absent parts 65 without having to cut the materials and significantly simplify the structure to facilitate the manufacture.

In this case, the liquid impervious film 64 of the leg gathers 60 is preferably extended from one leg gather 60 through the back side of the absorber 56 to the other leg gather 60 as in the mode illustrated in FIGS. 3 and 4 to ensure not only the water-shielding performance of the leg gathers 60 but also the water-shielding performance of the back side of the absorber 56. Alternatively, the liquid impervious film 64 contained in the leg gathers 60 and the liquid impervious film 11 covering the back side of the absorber 56 may be separately provided as in the mode illustrated in FIGS. 8 and 9. In the latter case, the material for the liquid impervious film 64 contained in the leg gathers 60 and the material 11 for the liquid pervious film covering the back side of the absorber 56 may be identical or different.

Similarly, the gather sheet 66 is preferably formed from an integral sheet ranging from one leg gather 60 through the back side of the absorber 56 to the other leg gather 60 as in the mode illustrated in FIGS. 3 and 4 to obtain the cloth-like outer surface without having to provide separately the crotch portion cover sheet as described above. Alternatively, the gather sheet 66 and the crotch portion cover sheet 12M may be separately provided as in the mode illustrated in FIGS. 8 and 9.

As another structure of the leg gathers 60, as in the mode illustrated in FIGS. 8 and 9, the leg gathers 60 may have attachment parts 68 that are fixed to the back side of the inner body 200, extension parts 69 that are extended from the attachment parts 68 to the surfaces of side parts of the inner body 200 so as to wrap around the lateral sides of the inner body 200, fallen parts 69B that are formed by fixing front-back both end portions of the extension parts 69 in a fallen state to the surfaces of the side parts of the inner body 200, free parts 69F that are formed by not fixing intermediate portions of the fallen parts in the extension parts, and elastically stretchable gather materials 63 that are fixed in an extended state along the front-back direction to at least forward end portions of the free parts 69F. In the leg gathers 60, the free parts 69F stand toward the legs as shown by two-dot chain lines in FIG. 9 from the boundaries with the attachment parts 68 as base ends due to the contraction of the elastically stretchable gather materials 63.

In this structure, the sections where the non-woven fabric absent parts 65 are to be provided can be decided as appropriate. However, the non-woven fabric absent parts 65 are preferably provided only in the portions of the extension parts 69 opposed to the surfaces of the side parts of the inner body 200 to make the liquid impervious film 64 exposed to the inside less prone to contact the skin.

In the mode illustrated in FIGS. 8 and 9, the top sheet 30 is folded toward the back side of the absorber 56 along the side edges of the absorber 56, and the separate gather sheet 66 is stuck to the inside non-woven fabric layer 61 nearer the base end side than the non-woven fabric absent parts 65. Alternatively, as in the mode illustrated in FIGS. 3 and 4, the width-direction both sides of the top sheet 30 may be extended to constitute the inside non-woven fabric layer 61 nearer the base end side than the non-woven fabric absent parts 65.

In the mode illustrated in FIGS. 8 and 9, the extension parts 69 of the leg gathers 60 are composed of a root-side portion extending toward the width-direction central side and a forward end-side portion that is folded toward the width-direction outside from the forward end of the root-side portion. Alternatively, the extension parts 69 may not be folded toward the width-direction outside but may be composed of only the portion extending toward the width-direction central side (not illustrated).

Meanwhile, in the front-back intermediate regions of the leg gathers 60 as standing portions, the inside non-woven fabric layer 61 and the outside non-woven fabric layer 62 can be stuck together and the elastically stretchable gather materials 63 sandwiched between the inside non-woven fabric layer 61 and the outside non-woven fabric layer 62 can be fixed by at least one of a hot-melt adhesive used in various application methods and a fixing means for material welding such as heat sealing or ultrasound sealing. Since sticking together entirely the inside non-woven fabric layer 61 and the outside non-woven fabric layer 62 deteriorates flexibility, the inside non-woven fabric layer 61 and the outside non-woven fabric layer 62 are preferably not bonded or are weakly bonded at the portions other than the bonding portions of the elastically stretchable gather materials 63. In the illustrated mode, by applying a hot-melt adhesive only to the outer peripheral surfaces of the elastically stretchable gather materials 63 by an application means such as a comb gun or a sure-wrap nozzle and sandwiching the elastically stretchable gather materials 63 between the inside non-woven fabric layer 61 and the outside non-woven fabric layer 62, the elongated resilient and elastic members are fixed to the inside non-woven fabric layer 61 and the outside non-woven fabric layer 62 and the inside non-woven fabric layer 61 and the outside non-woven fabric layer 62 are fixed to each other at the same time only by the hot-melt adhesive applied only to the outer peripheral surfaces of the elastically stretchable gather materials 63.

In the non-standing portions of the leg gathers 60 on the front-back both sides, the inside non-woven fabric layer 61 and the outside non-woven fabric layer 62 can be stuck together, the leg gathers 60 can be fixed to the front-side outer body 12F and the back-side outer body 12B in the mode illustrated in FIGS. 1 to 7, and the root-side portions and the forward end-side portions of the leg gathers 60 can be fixed and the leg gathers 60 can be fixed to the surfaces of the side parts of the inner body 200 in the mode illustrated in FIGS. 8 and 9 by at least one of a hot-melt adhesive used in various application methods and a fixation means 67 for material welding such as heat sealing or ultrasonic sealing. In the illustrated mode, the hot-melt adhesive and the fixation means 67 for material welding are combined. However, the foregoing fixations can be made by only either of the two means.

The dimensions of the leg gathers 60 can be decided as appropriate. In the case of a diaper for babies and infants, the standing height of the leg gathers 60 (width-direction spacing between the forward end and the base end in the unfolded state) is preferably 15 to 60 mm, in particular 20 to 40 mm.

In the foregoing modes, the materials for the inside non-woven fabric layer 61 and the outside non-woven fabric layer 62 are preferably flexible non-woven fabric excellent in uniformity and sealing performance such as spun-bonded non-woven fabric (SS or SSS), SMS non-woven fabric (SMS or SSMMS), or melt-blown non-woven fabric, that may be subjected as necessary to water-repellent treatment by silicon or the like. The fiber basis weight of the material is preferably about 10 to 30 g/m$^2$. In the mode illustrated in FIGS. 3 and 4, as seen from the fact that the inside non-woven fabric layer 61 nearer the base end side than the non-woven fabric absent parts 65 is formed from the top sheet 30, the material for the inside non-woven fabric layer 61 and the material for the outside non-woven fabric layer 62 may be partially different. Alternatively, the material for the inside non-woven fabric layer 61 and the material for the outside non-woven fabric layer 62 may be completely different.

In the foregoing modes, the elastically stretchable gather materials 63 may be elongated resilient and elastic members such as thread-shaped rubber or belt-shaped rubber. In the case of using rubber threads, the thickness is preferably 470 to 1240 dtex, more preferably 620 to 940 dtex. The stretch rate at the time of fixation is preferably 150 to 350%, more preferably 200 to 300%.

In the foregoing modes, the leg gathers 60 are provided in one each row on the right and left sides. Alternatively, the leg gathers 60 may be provided in two or more rows on the right and left sides.

DESCRIPTIONS OF THE TERMS USED HEREIN

Unless otherwise specified herein, the terms used herein have the meanings described below.

The "front-back (vertical) direction" refers to the direction linking the ventral side (front side) and the back side (rear side), and the "width direction" refers to the direction (right-left direction) orthogonal to the front-back direction.

The "extension ratio" refers to a value with respect to 100% representing the natural length.

The "gel strength" is measured in such a manner as described below. That is, a high-absorbent polymer of 1.0 g is added to an artificial urine of 49.0 g (urea: 20 wt %, salt: 8 wt %, calcium chloride dihydrate 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

The "basis weight" is measured in such a manner as described below. That is, a sample or a test piece is preliminarily dried and left stand in a test room or a test device in a standard state (at a temperature of 20±5° C. and a relative humidity of 65% or less) until reaching a constant weight. The preliminary drying refers to turning the sample or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) sample by the use of a cutting template (200 mm×250 mm±2 mm). The weight of the sample is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm² and the pressure area is 2 cm²).

The water absorption capacity is measured by carrying out JIS K7223-1996 "Testing method for water absorption capacity of super absorbent polymers."

The water absorption rate is determined as "time that elapses before the end point" by carrying out JIS K7224-1996 "Testing method for water absorption rate of super absorbent polymers" using 2 g of high absorbent polymer and 50 g of saline.

INDUSTRIAL APPLICABILITY

The present invention is usable to underpants-type disposable diapers as in the foregoing examples.

REFERENCE SIGNS LIST

11 Liquid impervious film
12 Outer body
12A Side seal portion
12B Back-side outer body
12F Front-side outer body
30 Top sheet
40 Intermediate sheet
50 Absorbent element
56 Absorber
58 Package sheet
60 Leg gather
61 Inside non-woven fabric layer
62 Outside non-woven fabric layer
63 Elastically stretchable gather material
64 Liquid impervious film
65 Non-woven fabric absent part
66 Gather sheet
66r Folded portion
200 Inner body

The invention claimed is:

1. An underpants-type disposable diaper, comprising:
an outer body that forms individually or integrally a front body and a back body;
an inner body that has an absorber and is attached to an inner surface of the outer body extending from the front body to the back body through a crotch portion; and
leg gathers, having standing parts configured to extend toward the legs of a wearer in a standing state, that extend along both sides of an absorption surface of the inner body of the absorption surface in a width direction, the outer body being joined together at both side edges at the front body and the back body to form a waist opening and a pair of right and left leg openings, wherein
the leg gathers have:
an inside non-woven fabric layer constituting an inner surface in the width direction in the standing state;
an outside non-woven fabric layer constituting an outer surface in the width direction in the standing state;
elastically stretchable gather members that are provided along a front-back direction between the inside non-woven fabric layer and the outside non-woven fabric layer at at least forward end portions of the leg gathers in intermediate portions of the leg gathers in the front-back direction; and
a liquid impervious film that is sandwiched between the inside non-woven fabric layer and the outside non-woven fabric layer in an area ranging from a base end-side to a forward end-side thereof, wherein
parts of the leg gathers that are provided with the liquid impervious film and that is closer to the base end-side than the forward end-side constitute non-woven fabric absent parts where the inside non-woven fabric layer does not exist and the liquid impervious film is exposed through the entire leg gathers in the front-back direction, the underpants-type disposable diaper further comprises:

a liquid pervious top sheet provided on a front surface side of the absorber and on the inner surface of the standing parts of the leg gathers, the liquid pervious top sheet being formed of non-woven fabric extending to the base end-side of the standing parts of the leg gathers beyond both sides of the absorber in the width direction, extended parts of the liquid pervious top sheet extending via the base end of the standing parts of the leg gathers and forming a part of the inner surface of the standing parts of the leg gathers, a gather sheet provided on a back surface side of the inner body, the gather sheet being formed of non-woven fabric extending beyond the liquid pervious top sheet on both sides of the absorber in the width direction, wherein both end portions of the gather sheet in the width direction are folded to form folded portions, and forward ends of the folded portions are separated from the extended parts of the liquid pervious top sheet, the liquid impervious film is provided at least from a portion between the folded portions of the gather sheet to a portion between the liquid pervious top sheet and the gather sheet, and the outside non-woven fabric layer is formed by a portion of the gather sheet other than the folded portion, the inside non-woven fabric layer is formed by the folded portions of the gather sheet and the extended parts of the liquid pervious top sheet, and the non-woven fabric absent parts are formed as a separated area between the folded portions of the gather sheet and the extended parts of the liquid pervious top sheet.

2. The underpants-type disposable diaper according to claim 1, wherein a plurality of elastically stretchable gather members are provided at intervals in a direction from the forward end-side to the base end-side, and the non-woven fabric absent parts are formed only between the elastically stretchable gather members.

3. The underpants-type disposable diaper according to claim 1, wherein the outer body includes separately a front-side outer body constituting the front body and a back-side outer body constituting the back body, the front-side outer body and the back-side outer body being not continuous but separated from each other at a crotch portion side, the leg gathers extend from a fixed section of the inner body with respect to the front-side outer body to a fixed section of the inner body with respect to the back-side outer body, and the leg gathers are extended to lateral sides of the inner body, front end portions of the leg gathers are set as fixation portions fixed to an inner surface of the front-side outer body, back end portions of the leg gathers are set as fixation portions fixed to an inner surface of the back-side outer body, and the fixation portions of the front end portions and the fixation portions of the back end portions are contracted in a width direction by resilient and elastic members provided in the front-side outer body and the back-side outer body.

4. The underpants-type disposable diaper according to claim 1, wherein the liquid impervious film is extended from one leg gather to another leg gather through the back surface side of the absorber.

5. The underpants-type disposable diaper according to claim 1, wherein the leg gathers include:

attachment parts that are fixed to the back side of the inner body;

extension parts that are extended from the attachment parts to surfaces of side parts of the inner body so as to wrap around the lateral sides of the inner body;

fallen parts that are formed by fixing both end portions of the extension parts in the front-back direction in a fallen state to the surfaces of the side parts of the inner body;

free parts that are formed by not fixing intermediate portions of the fallen parts in the extension parts; and elastically stretchable gather members that are fixed in an extended state along the front-back direction to at least forward end portions of the free parts, and the non-woven fabric absent parts are formed only in the portions of the extended parts opposed to the surfaces of the side part of the inner body.

* * * * *